(12) United States Patent
Rodriquez et al.

(10) Patent No.: US 10,668,544 B2
(45) Date of Patent: Jun. 2, 2020

(54) EMERGENCY ROOM RING CRACKER AND CUTTER

(71) Applicants: Gerardo Rodriquez, APO, AE (US); Sergio Rucci, Victor, NY (US)

(72) Inventors: Gerardo Rodriquez, APO, AE (US); Sergio Rucci, Victor, NY (US)

( * ) Notice: Subject to any disclaimer, the term of this patent is extended or adjusted under 35 U.S.C. 154(b) by 0 days.

(21) Appl. No.: 16/280,015

(22) Filed: Feb. 19, 2019

(65) Prior Publication Data
US 2019/0255630 A1    Aug. 22, 2019

Related U.S. Application Data

(60) Provisional application No. 62/632,391, filed on Feb. 19, 2018.

(51) Int. Cl.
| | |
|---|---|
| *B23D 29/02* | (2006.01) |
| *A61B 90/00* | (2016.01) |
| *B25B 7/12* | (2006.01) |
| *B25B 7/02* | (2006.01) |

(52) U.S. Cl.
CPC .............. *B23D 29/02* (2013.01); *A61B 90/03* (2016.02); *B25B 7/02* (2013.01); *B25B 7/12* (2013.01); *A61B 2090/033* (2016.02); *A61B 2090/08021* (2016.02)

(58) Field of Classification Search
CPC ..................... B23D 29/02; A61B 90/03; A61B 2090/08021; A61B 2090/033; B25B 7/02; B26B 7/12

USPC ........................................................... 30/175
See application file for complete search history.

(56) References Cited

U.S. PATENT DOCUMENTS

| | | | | |
|---|---|---|---|---|
| 1,867,342 | A * | 7/1932 | Wieg ..................... | B23D 45/16 30/124 |
| 4,976,034 | A * | 12/1990 | Whitman .............. | B23D 45/003 30/124 |
| 5,365,625 | A * | 11/1994 | Han ........................ | A61B 17/00 7/158 |
| 6,425,183 | B2 * | 7/2002 | Lemmens .............. | B23D 27/02 30/142 |
| 6,925,917 | B2 * | 8/2005 | Tilley ................... | B23D 45/003 30/123.3 |
| 9,808,052 | B1 * | 11/2017 | Mouzakis, III ........... | B25B 7/02 |
| 9,889,569 | B2 * | 2/2018 | Al Modhen ............ | B26B 17/00 |

(Continued)

*Primary Examiner* — Hwei-Siu C Payer
(74) *Attorney, Agent, or Firm* — Duncan Palmatier

(57) ABSTRACT

The present invention discloses a ring cutter and ring cracker intended for use by medical personnel. The ring cutter employs a tissue guard that slips under the ring to protect the patient's finger or other appendage. A clipper head is inserted into the tissue guard. The tissue guard does not move and prevents the jaws of the clipper from injuring the patient. The tissue guard may be constructed of plastic that will break away after use to prevent contamination between patients. The invention also incorporates a ring cracker for breaking tungsten or ceramic rings. A recess in a ring base in one of the arms of the ring clipper retains a part of a ring. In the other arm, a threaded bolt with a hardened tip extends toward the ring. The arms of the clipper can be locked by a bar in a fixed position. A knob on the bolt allows a hardened tip at the end of the bolt to exert pressure on the tungsten or ceramic ring until it cracks, without injury to the patient.

10 Claims, 5 Drawing Sheets

(56) References Cited

U.S. PATENT DOCUMENTS

| | | | |
|---|---|---|---|
| 2012/0060376 A1* | 3/2012 | Polofsky | B25B 7/12 30/177 |
| 2013/0318800 A1* | 12/2013 | Weiss | B23D 45/003 30/370 |
| 2019/0255630 A1* | 8/2019 | Rodriquez | A61B 90/03 |
| 2019/0308337 A1* | 10/2019 | Swanstrom | B26B 29/04 |

* cited by examiner

EMERGENCY ROOM RING CRACKER AND CUTTER

CLAIM OF PRIORITY TO PROVISIONAL APPLICATION (35 U.S.C. § 119(e))

This application claims priority under 35 U.S.C. § 119(e) from provisional patent Application No. 62/632,391 filed on Feb. 19, 2018. The 62/632,391 application is incorporated herein by reference.

FIELD OF THE INVENTION

The present invention relates to a tool to crack or cut rings in order to remove the ring a from a finger or other appendage. The invention is intended for use by emergency medical technicians, nurses, and doctors as a fast, safe, reliable and cost effective means to remove rings that cannot be slid from the finger and are causing medical problems or interfering with medical treatment.

BACKGROUND OF THE INVENTION

Rings often become stuck and cannot be slipped off a finger, even with lubricants. In some cases, the finger may swell and the ring will pose a medical risk to the wearer as blood in the finger is trapped. In other cases, limb injuries or infection can cause swelling or dependent oedema in fingers which may be exacerbated by the presence of a ring. Similarly, metal rings are sometimes placed on other appendages, such as a male penis, become stuck, and require cutting to remove. In yet other cases, the ring that cannot be slipped off may pose risks to an unconscious patient or interfere with medical treatment.

A number of ring cutting tools have been developed. A common tool is the Esslinger ring cutter, formed in the general shape of pliers, which slips a protective guide between the ring and the finger, then levers a cutting wheel onto the ring. The cutting wheel can be turned by hand or by an electric powered tool. The protective guide prevents the cutting wheel from cutting the finger. A disadvantage of this type of ring cutter is that the ring gets very hot as the wheel cuts through the ring. The heat is transferred to the ring which can in turn burn the finger. Another disadvantage of this type of ring cutter is that it is less effective in cutting through hard metals, such as stainless steel, titanium and cobalt, materials that are not uncommon in rings. Because these hard metals require more time to cut through, the problem of heat transfer is greater.

Another problem with existing ring cutters is they are not practical for removing rings made of very hard materials, such as tungsten and ceramics. However, tungsten and ceramic rings are brittle and can be "cracked" by exerting pressure on one part of the ring. An example of a device for removing tungsten rings is the Tungsten Finger Ring Removal Tool sold by VP Gabriel, Inc. This tool surrounds the finger with a frame and uses a type of vice that squeezes the tungsten ring until it shatters. A disadvantage of this tool is that the frame makes it difficult to use when there is insufficient room to maneuver the tool around the patient's hand. Another disadvantage is that the tool only works on tungsten rings, so is useful in only a limited number of cases and is not practical in emergency medical services with limited space for equipment.

Needed is a tool that can remove rings without causing damage to the patient through heat transfer or accidental cutting. Also needed is tool that can remove rings constructed of hard materials, such as tungsten or ceramic.

SUMMARY OF THE INVENTION

The present invention discloses a ring remover and ring cracker that avoids the problem of heat transfer by using a levered ring clipper, rather than a cutting wheel, and incorporates a ring cracker for tungsten or ceramic rings. The invention employs a tissue guard that slips under the ring to protect the patient's finger or appendage. The clipper head is inserted into the tissue guard. The tissue guard is does not move and prevents the cutting parts of the clipper from reaching the patient's skin. In a preferred embodiment, after cutting the ring, the tissue guard will break away and have to be replaced for another use.

The invention also incorporates a ring cracker for breaking tungsten or ceramic rings. In one of the arms of the ring clipper, a recess is configured to retain part of a ring. In the other arm, a threaded bolt with a hardened tip extends toward the ring. The arms of the clipper can be locked in a fixed position. A knob on the threaded bolt can be turned so that the hardened tip exerts pressure on the tungsten or ceramic ring until the ring cracks, without injury to the patient.

The invention is intended for use by emergency medical technicians, nurses, and doctors as a fast, safe, reliable and cost effective means to remove rings from patients' fingers. By combining a ring cutter and cracker in a single tool, the invention increases capability to medical personnel, especially when space for equipment is limited, as in mobile emergency medical service vehicles or small hospitals.

DETAILED DESCRIPTION

Figure 1:
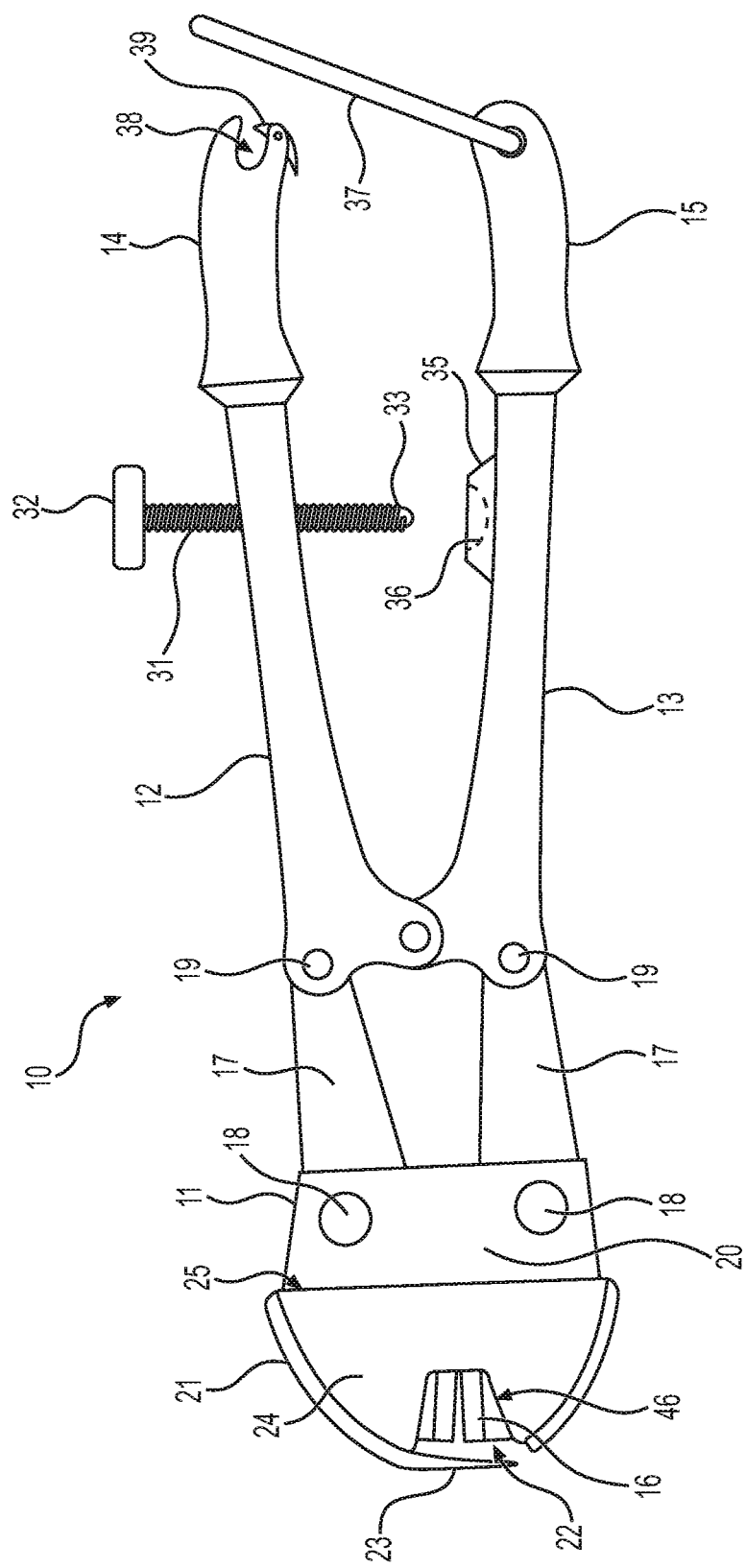
FIG. 1 is side view of the ring cracker and cutter of the present invention.

FIG. 1 shows an embodiment of the combined ring remover 10 of the present invention. The ring clipper head 11 has a pair of hardened metal jaws forming jaw blades 16 that pivot at a jaw joint fulcrum 20 on pins or bolts 18 and connect through extensions 17 to top and bottom articulated joints 19 and then to top 12 and bottom 13 lever handles. The handles, 12 and 13, have top 14 and bottom 15 grips. When the handles, 12 and 13, are spread apart, the jaws 16 are opened, and when the handles, 12 and 13, are brought together, the jaw blades 16 close and come together under the tremendous force created by the articulation 19 of the levers, 12 and 13.

Figure 4:
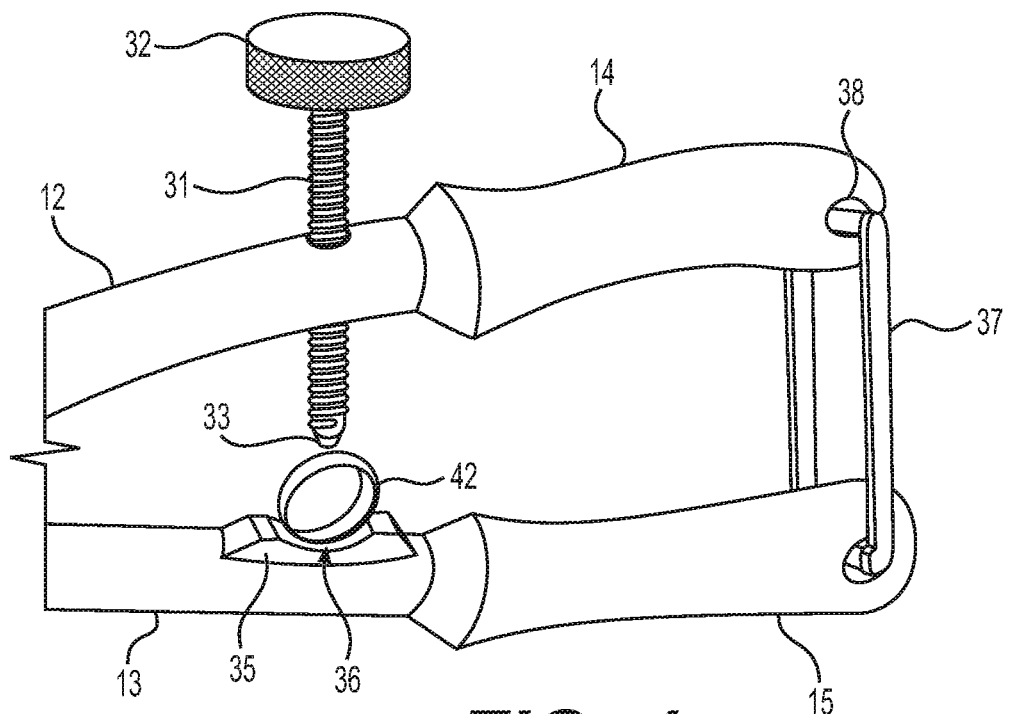
FIG. 4 is a side perspective view of the ring cracker portion of the invention.
Figure 5:
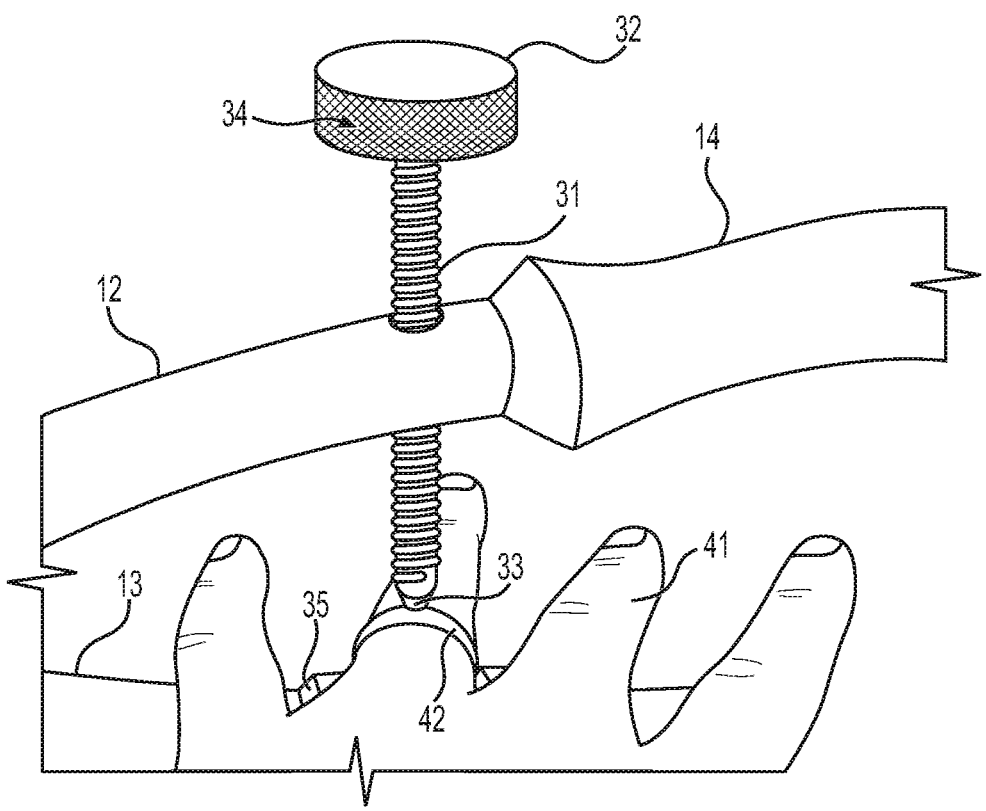
FIG. 5 is a side perspective view of the ring cracker portion of the invention in place to crack a ring off a finger.

In the top and bottom handle levers, 12 and 13, is a ring cracker for breaking tungsten and ceramic rings. On the bottom handle 13 is a ring retaining base 35 formed of hard metal with a curved groove 36 to hold a portion of a ring 42 (as shown in FIG. 5). A releaseable locking bar 37 extending from a first handle of the ring clipper to a second handle and securing the first and second handles at a fixed distance from each other. As shown in FIGS. 1 and 4, the retainer bar 37 swivels from the end of the bottom grip 15 of the bottom handle 13 and can be received by a retainer seat 38 in the end of the top grip 14 of the top handle 12 to hold the top and bottom handles, 12 and 13, in a fixed position (as shown in FIG. 4). In a preferred embodiment, a locking mechanism 39 releasably holds the retainer bar 37 in place. The threaded shaft of bolt 31 threads through a threaded bore (not shown) in the top handle 12, directly above the ring cracker base 35. The bolt 31 has a knob 32 at a knob end above the handle 12 to turn the bolt 31 in the threaded bore. In a preferred embodiment, the knob 32 may be knurled 34 (as shown in FIG. 5). At the opposite end of the bolt 31 is a ring cracking end with a hardened tip 33.

Figure 2:
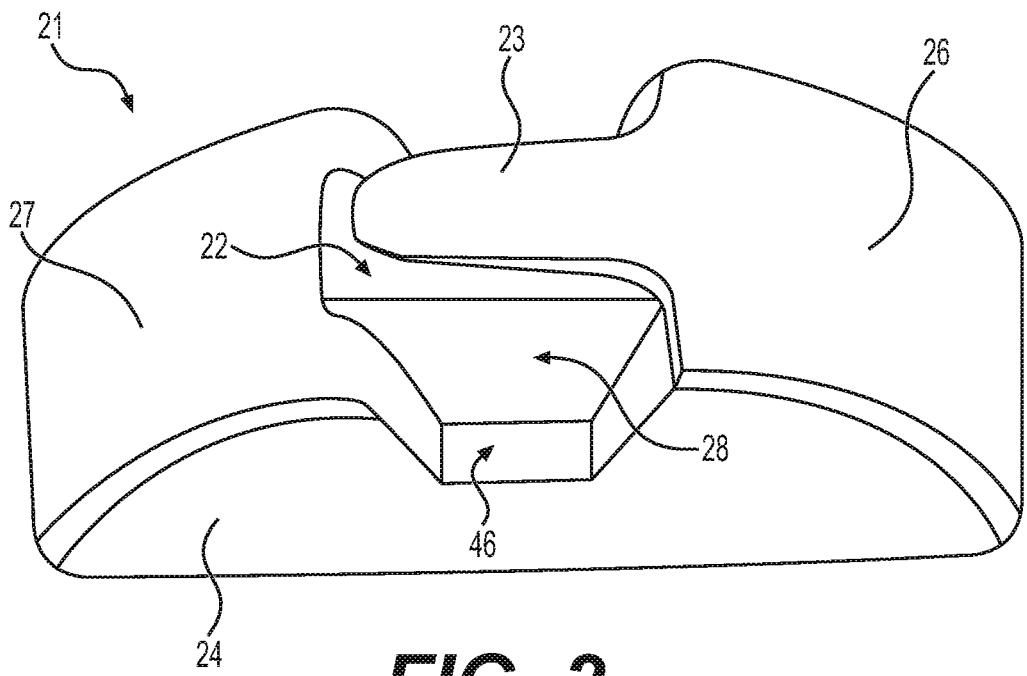
FIG. 2 is a top perspective view of the ring clipper tissue guard.
Figure 3:
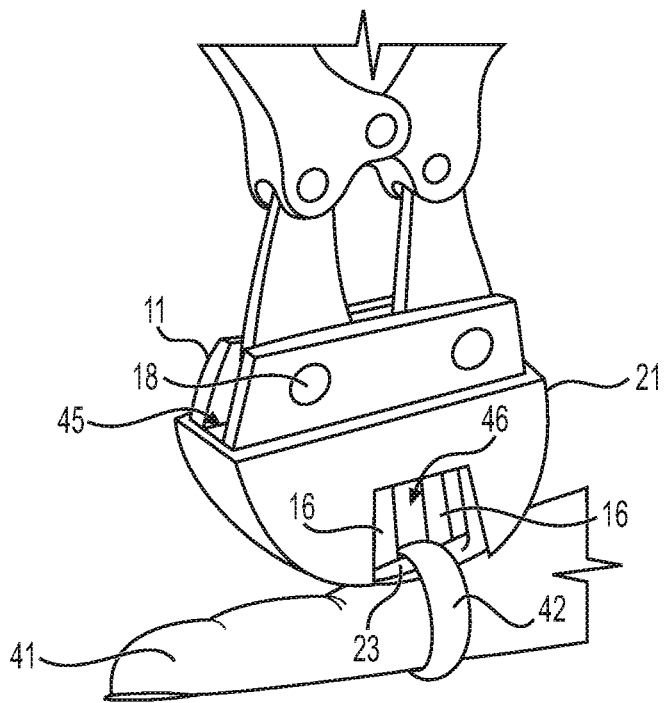
FIG. 3 is a side perspective view of the ring clipper and tissue guard in place to cut a ring off a finger.
Figure 6:
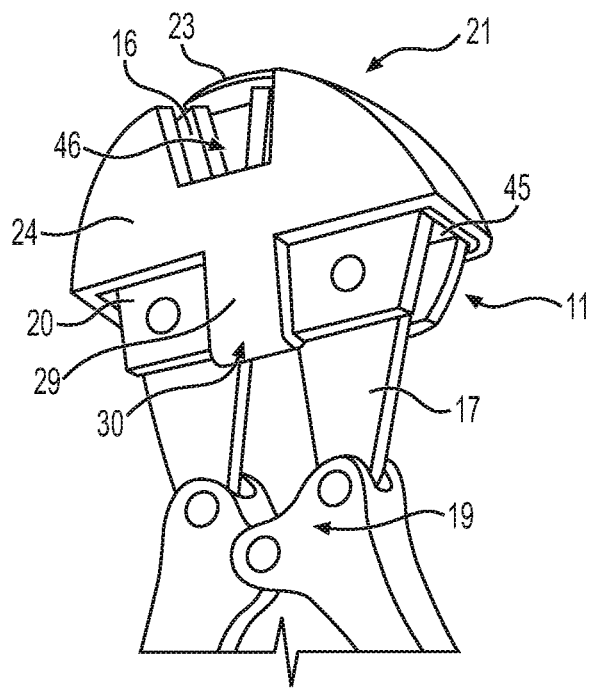
FIG. 6 is a three-quarter rear perspective view of the ring clipper tissue guard with a retainer clip.
Figure 7:
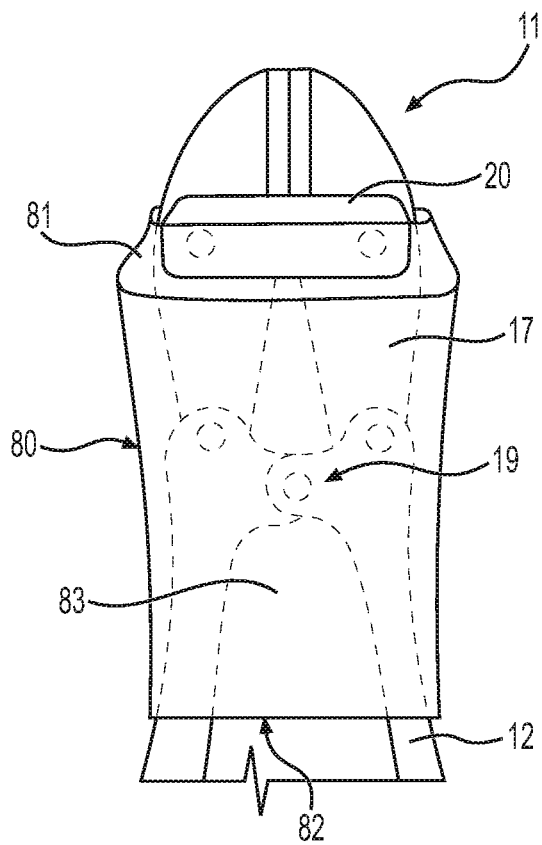
FIG. 7 is a side perspective view of the ring clipper with a prophylactic sleeve.

FIG. 2 provides a closer view of the ring cutter's tissue guard 21. The tissue guard 21 is shaped to fit snugly over the clipper head 11. The jaws of the clipper head 11 are formed by blades 16. Each blade 16 has opposing faces extending from the blade 16 to an edge opposite the blade 16, and each blade 16 has a blade tip end and a blade fulcrum end opposite the tip end. The tissue guard 21 has an interior space 28 formed by the bottom base 25, opposing sides 24, front 26, back 27, and open top 22. The base 25 has an opening 45 sized to receive the clipper head 11 within the interior space 28, with the tip ends of the blades 16 directed toward the open top 22 and the opposing faces of the blades 16 parallel to the opposing sides 24 of the tissue guard 21. The interior space 28 is sized to accommodate the clipper head 11 and allow the blades 16 to be spread apart and brought together within the interior space 28. In an alternative embodiment, shown in FIG. 6, the tissue guard may have a retainer 29 that extends down from one or both sides 24 of the tissue guard 21. The retainer 29 has a clip 30 at its bottom end to engage the lower ledge of the jaw joint 20 of the clipper head 11, thereby holding the tissue guard 21 in place. The clipper jaws 16 are inserted into a bottom opening 45 of the tissue guard 21 occupy an interior space 28 so that the jaw blades 16 may reach a ring 42 on a finger 41 (as shown in FIG. 3) or other appendage. A thin tissue guard tapered protective fang 23 extends from the front 26 of the tissue guard 21 over the top opening 22 toward the back 27. The fang 23 is disposed over the open top 22 of the tissue guard 21 with the fang's base end proximal to the front 26 of the tissue guard 21 and the fang tip end extending toward the back 27 of the tissue guard 21. A bottom surface of the fang 23 is directed into the interior space 28 of the tissue guard and a top surface of the fang 23 faces away from the interior space 28. The fang 23 is slipped between a ring 42 and a finger 41 or other appendage, such as a male penis (not shown), which will reside at a mid-section of the fang 23 between the fang's base and tip ends. A detent in the bottom surface of the mid-section of the fang 23, such as the detent 73 shown in FIG. 9, can help keep the ring in the correct position. The bottom surface of the tapered fang 23 prevents the jaw blades 16 from reaching the finger 41.

FIG. 3 shows the ring cutter in place. The tissue guard fang 23 is tapered and smooth to fit between the ring 42 and finger 41, even when the space is very tight. The tissue guard 21 is put in place over the patient's finger 41 and under the ring 42, then the head 11 of the clipper is inserted into the interior space 28 of the tissue guard 21 and the lever handles, 12 and 13, are brought together to cut the ring 42. In the alternative embodiment shown in FIG. 6, a retainer 29 engages the jaw joint 20 to hold the clipper head 11 in place. In a preferred embodiment, the tissue guard 21 is made of a breakable plastic so that, after the ring is cut, the guard 21 may be broken and discarded. A new tissue guard 11 is then used for the next patient, avoiding the spread of contaminants between patients.

FIGS. 4 and 5 show the ring cracker in operation. The retainer bar 37 is swiveled into the seat 38 of the top grip 14 to hold the handles, 12 and 13, at a fixed distance from each other. A ring 42 is held in position by a groove 36 in the ring cracker base 35. The ring cracker bolt 31 is screwed down by turning its knob 32 until the hardened tip 33 just touches the ring 42. A little additional pressure on the ring 42 is added by turning the knob 32. Because tungsten and ceramic rings are very brittle, only a small force is required to cause the tungsten or ceramic to shatter and the ring to crack apart. FIG. 5 shows how the patient's finger 41 and hand fit between the handles, 12 and 13, during operation of the ring cracker.

In an additional embodiment, a prophylactic sleeve 80 is placed over portions of the clipper head 11, the jaw joint 20, extensions 17, articulated joint 19, and portions of the lever handles, 12 and 13, to prevent contaminants from reaching these parts, thereby allowing reuse of the clipper without sterilization. The sleeve 80 has a bottom handle opening 82 through which the clipper head 11 is inserted until the jaw opening, or neck 81, of the sleeve covers all or portions of the jaw blades 16 and jaw joint 20, and the sleeve body 83 covers and protects the remaining parts. The sleeve 80 may be made of a soft and flexible non-porous material, or it may be a flexible but semi-rigid and non-porous body 83 with a dual-durometer baffled neck 81 that conforms and clings to the clipper head 11. The tissue guard 21 is placed over the clipper head 11 and the neck 81 of the sleeve 80. A semi-ridged sleeve body 83 may also incorporate a ledge near the neck 81 to accept the retainer clip 29 shown in FIG. 6. The sleeve 80 may be cleaned or discarded and replaced.

Figure 8:
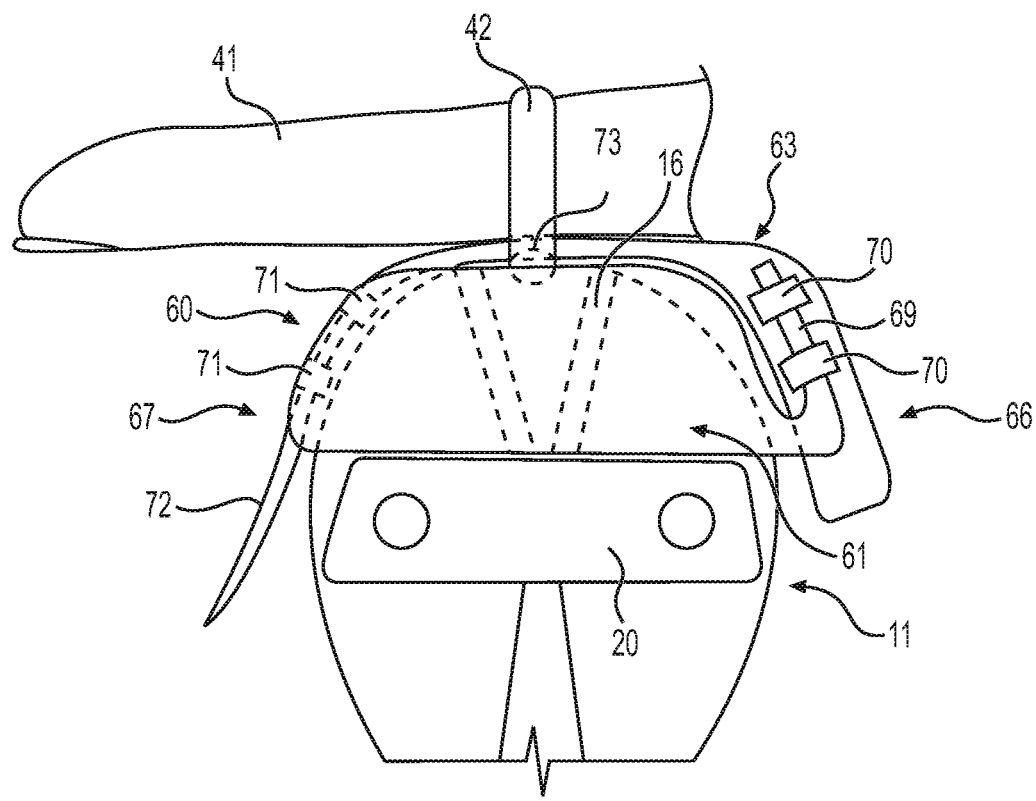
FIG. 8 is a side perspective view of an alternative embodiment of the ring clipper tissue guard system.
Figure 9:
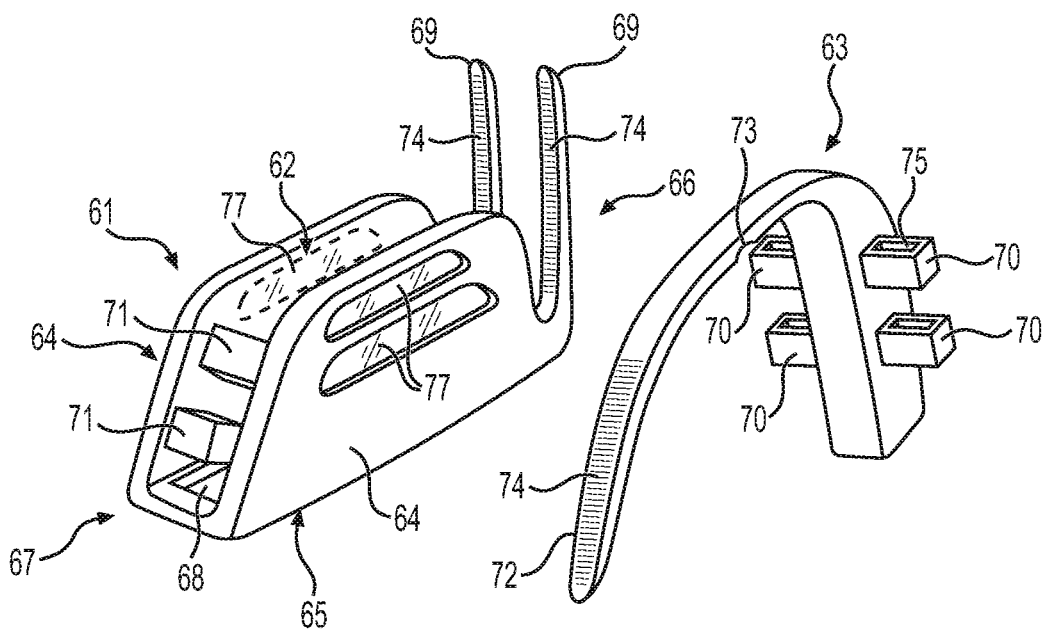
FIG. 9 is an exploded side view of the alternative embodiment of the ring clipper tissue guard system.

An alternative embodiment for a tissue guard system 60 is shown in FIGS. 8 and 9. This system 60 uses a separate protective fang member 63 and clipper housing 61. The fang member has an extended fang strap 72 that is slipped between a ring 42 and appendage 41. A detent 73 in the fang strap 72 helps locate the fang member 63 in the correct position. Ratcheting retainers 70 on the sides of the fang strap 72 receive straps 69 at the front 66 of the clipper housing 61 through passages 75. The tissue guard straps 69 have one-way ramps 74 and the ratcheting retainers 70 have internal lever mechanisms (not shown) that cinch the protective fang member 63 to the housing 61 and prevent it from backing out. This arrangement is familiar as that used commonly in "zip-ties" or "electrical ties". If necessary, excess strap 69 material can be cut off. Similar to the tissue guard straps 69, the fang strap 72 has one-way ramps 74 so that, when it is inserted into the clipper housing 61 receivers 71 at the rear 67 of the housing 61, internal lever mechanisms (not shown) in the receivers 71 cinch the fang strap 72 into position.

In operation, the fang strap 72 of member 63 is slipped between a ring 42 and finger 41 or other appendage until the detent 73 in the fang strap 72 locates the fang member 63 in the correct position. The tissue housing 61 may be placed on a ring clipper head 11 through the housing's 61 bottom opening 68 before or after being secured to the fang member 63. As described above in connection with FIG. 6, the housing 61 may have retainers 29 extending down from the bottom 65 of the sides 64 to engage the lower ledge of the jaw joint 20, thereby holding the housing 61 in place over the clipper head 11. The fang member 63 is secured to the clipper 11 with the housing 61 over the top opening 62 by inserting the fang strap 72 into the housing receivers 71, inserting the housing's 61 straps 69 into the fang member's 63 receivers 70, and cinching the straps, 69 and 72, into position. Alternatively, after the fang member 63 is positioned between the ring 42 and finger 41, the housing 61 may be connected to the fang member 63 before inserting the clipper head 11 into the housing 61. The straps, 69 and 72, are connected to the receivers, 70 and 71, as described above. The clipper head 11 is then inserted into the opening 68 in the bottom 65 of the housing to bring the jaw blades 16 into position to cut the ring 42. As discussed above, retainers 29 (shown in FIG. 6) can secure the housing 61 to the clipper head 11. Windows 77 in the sides 64 of the housing 61 provide visual access to the position of the clipper's 11 jaw blades 16. The windows 77 may be openings in the housing's 61 sides 64, or they may clear ports allowing visual access to the jaws 16. Such windows 77 are also adaptable to the tissue guard 21 described above as substitutes for, or in addition to, the openings 46 shown in FIG. 2. Once in position, bringing together the handles, 12 and 13, will close the jaw blades 16 and clip the ring 42.

The drawings and description set forth here represent only some embodiments of the invention. After considering these, skilled persons will understand that there are many ways to make an emergency room ring cracker and cutter according to the principles disclosed. The inventor contemplates that the use of alternative structures, materials, or manufacturing techniques, which result in a ring cracker and cutter according to the principles disclosed, will be within the scope of the invention.

The invention claimed is:

1. A ring remover comprising:
    a ring clipper comprising jaws connected to handles, each jaw comprising a blade and opposing faces extending from the blade to an opposite edge, wherein each blade has a tip end and a fulcrum end opposite the tip end, and wherein the blades of the jaws can be spread apart and brought together about a fulcrum by the handles,
    a tissue guard comprising a base, opposing sides extending up from the base, a front, a back, an open top, and an interior space formed by the base, the opposing sides, the front, the back and the open top, the base comprising an opening sized to receive the jaws of the ring clipper within the interior space with the tip ends of the blades directed toward the open top and the opposing faces of the jaws parallel to the opposing sides of the tissue guard, and wherein the interior space is sized to accommodate the blades and allow the blades to be spread apart and brought together within the interior space,
    a protective fang having a fang tip end and a fang base end, wherein the fang is disposed over the open top of the tissue guard with the fang base end proximal to the front of the tissue guard and the fang tip end extending toward the back of the tissue guard, and
    wherein the protective fang is adapted to fit between a ring and an appendage on which the ring is worn and is further adapted to bring the blades in contact with the ring.

2. The ring remover of claim 1 wherein the tissue guard further comprises a window in at least one of the opposing sides, wherein the window allows the blades of the ring clipper to be seen as the blades come in contact with the ring.

3. The ring remover of claim 1 wherein the protective fang tapers from the fang base end to the fang tip end.

4. The ring remover of claim 1 wherein the protective fang further comprises a mid-section between the fang base end and the fang tip end, and further comprises a bottom surface facing the interior space of the tissue guard, wherein the bottom surface further comprises a detent to receive the ring.

5. The ring remover of claim 1 wherein the tissue guard further comprises a retainer clip extending down below the base from at least one of the opposing sides, wherein the retainer clip engages with a clip receiver on the ring clipper to secure the tissue guard to the ring clipper.

6. The ring remover of claim 1 further comprising a prophylactic sleeve having a jaw opening at a first end of the sleeve and a handle opening at a second end of the sleeve opposite the first end, wherein the prophylactic sleeve is disposed over the ring clipper so that the jaw opening covers the fulcrum end and the handle opening covers at least a portion of the handles, and wherein the opening of the base of the tissue guard covers at least a portion of the jaw opening of the prophylactic sleeve.

7. The ring remover of claim 1 wherein:
    the tissue guard further comprises a housing having a mounting strap member at the front of the tissue guard and a retaining block member at the back of the tissue guard,
    the fang further comprises a retaining block portion at the fang base end, a mounting strap portion at the fang tip end, and the protective fang further comprises a ring-retaining portion between the retaining block portion and the mounting strap portion,
    wherein the mounting strap portion of the fang tip end is received by and secured to the retaining block member of the tissue guard, the mounting strap member of the tissue guard is received by and secured to the retaining block portion of the fang base end, and wherein the ring fits within the ring-retaining portion of the protective fang.

8. The ring remover of claim 1 further comprising a ring cracker comprising:
    a releaseable locking bar extending from a first one of the handles of the ring clipper to a second one of the handles to secure the handles at a fixed distance from each other,
    a threaded shaft received by a threaded bore in one of the handles, the threaded shaft having a knob end and a ring cracking end opposite the knob end, wherein the ring cracking end is directed toward the other of the handles, and
    a ring retaining base disposed on the other of the handles and oriented toward the ring cracking end of the threaded shaft.

9. A tissue guard for a ring clipper comprising:
    a housing comprising a base, opposing sides extending up from the base, a front portion, a rear portion opposite the front portion, an open top portion, and an interior space formed by the base, the opposing sides, the front portion, the rear portion and the open top portion, the base further comprising an opening sized to receive jaws of a ring clipper within the interior space, at least one mounting member at the front portion and at least one retaining member at the rear portion, wherein the interior space is sized to accommodate the jaws and allow the jaws to spread apart and come together within the interior space, a protective member comprising a mounting portion, a mid-portion and a retaining portion, wherein the mounting portion is received by and secured to the mounting member of the housing, the retaining portion is received by and secured to the retaining member of the housing, and the mid-portion is disposed over the open top portion of the housing, and wherein the mid-portion of the protective member is adapted to fit between a ring and an appendage on which the ring is worn and is further adapted to bring the jaws of the ring clipper in contact with the ring.

10. The tissue guard of claim 9 wherein the mounting portion of the protective member and the mounting member of the housing comprise a one-way ratcheting mechanism.

\* \* \* \* \*